US 6,748,256 B2
United States Patent
Brodnick et al.
Date of Patent: Jun. 8, 2004

(54) PHYSIOLOGICAL-SIGNAL-ANALYSIS DEVICE HAVING A PLURALITY OF ELECTRODE LEADS

(75) Inventors: Donald E. Brodnick, Cedarburg, WI (US); Mark Kohls, New Berlin, WI (US); Carrie L. Kohls, New Berlin, WI (US); April K. Kohls, New Berlin, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 0 days.

(21) Appl. No.: 09/683,771

(22) Filed: Feb. 12, 2002

(65) Prior Publication Data

US 2003/0153840 A1 Aug. 14, 2003

(51) Int. Cl.$^7$ ................................ A61B 5/0408
(52) U.S. Cl. ........................ 600/382; 600/391
(58) Field of Search .................. 600/372–394, 600/508–521; 607/115, 142–156

(56) References Cited

U.S. PATENT DOCUMENTS 5,951,598 A * 9/1999 Bishay et al. ............... 607/142
6,246,907 B1 * 6/2001 Lin et al.
2003/0017743 A1 * 1/2003 Picardo et al. ............... 439/521

OTHER PUBLICATIONS

Marquette Electronics Classic 12–Lead electrode placement, form M01740DE0, published prior to Feb., 2001.
M.J. Goldman, Principles of Climical Electrocardiology, 11th edition, 1982, p. 3, 8–9, Lange Medical Publications, Los Altos, California.
P.W. Macfarlane & T.D. Veitch Lawrie, Comprehensive Electrocardiology, 1st edition 1989, p. 319, Pergamon Press, New York, New York.

P.M. Rautaharju et al., The Effect of Modified Limb Electrode Positions on Electrocardiographic Wave Amplitudes, p. 109–114, J. Electrodcardiology 1980.

P. Gamble, et al., A Comparison of the Standard 12–Lead Electrocardiogram to Exercise Electrode Placements, p. 616–622, vol. 85, May 1984 issue, Chest 1984.

D. Brodnick, BS, MS, A Method to Locate Electrode Placement, Journal of Electrocardiology, Supplement 2000, released Feb. 13, 2001, p. 211–218, vol. 33, Churchill Livingstone—A Harcourt Health Sciences Company.

* cited by examiner

Primary Examiner—Scott M. Getzow
(74) Attorney, Agent, or Firm—Michael Best & Friedrich LLP

(57) ABSTRACT

A physiological-signal-analysis device including a lead set connected to a central unit. The lead set includes a plurality of electrodes connectable to a patient. Each electrode has a non-alphanumeric symbol that defines a placement of the electrode on the patient in relation to the other electrodes. The lead set further includes a plurality of lead wires. Each lead wire is connected to one of the electrodes, respectively, and has a symbol that defines the electrode connected to the lead wire. The electrodes may be provided to an attendant as an electrode pack.

34 Claims, 6 Drawing Sheets

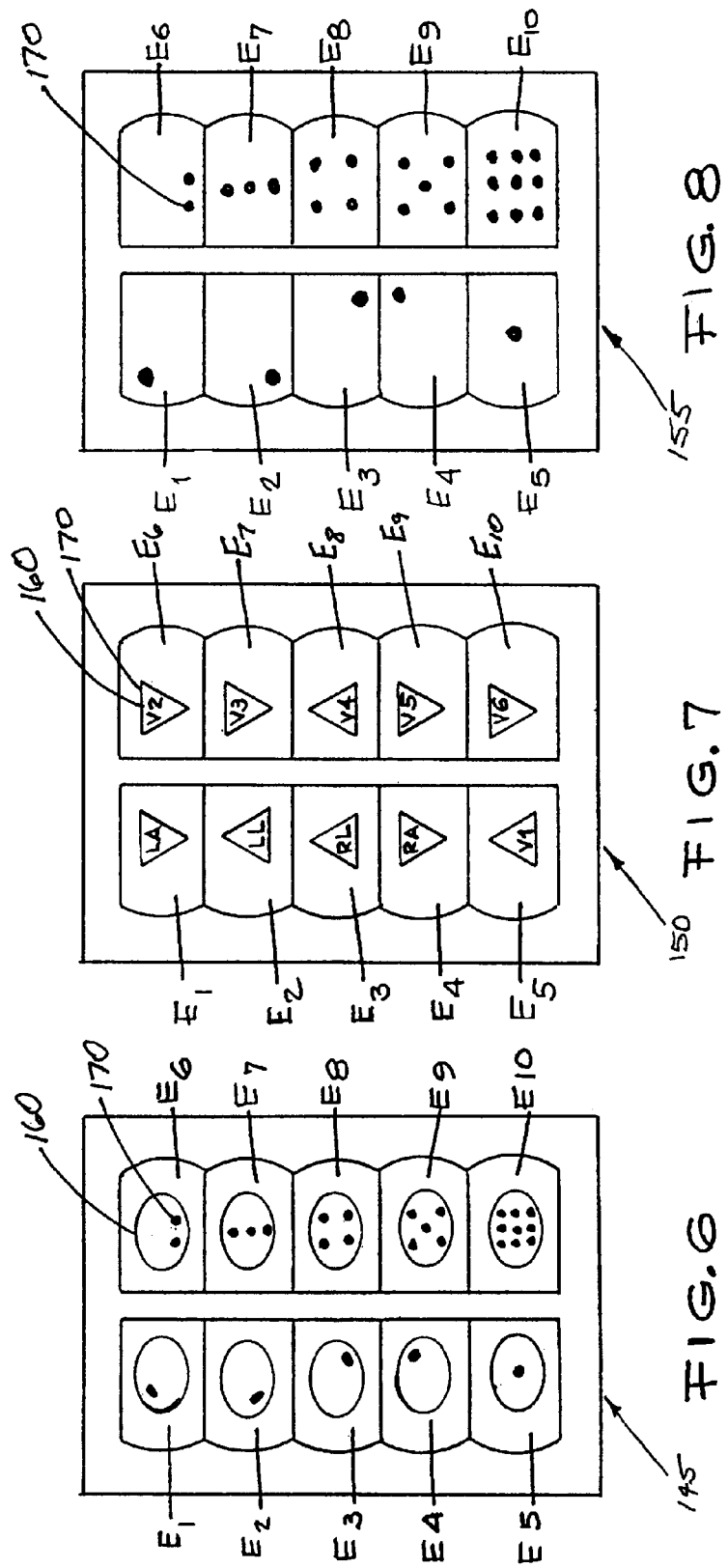

PHYSIOLOGICAL-SIGNAL-ANALYSIS DEVICE HAVING A PLURALITY OF ELECTRODE LEADS

BACKGROUND OF INVENTION

The invention relates to a physiological-signal-analysis device, and particularly to a physiological-signal-analysis device having a plurality of electrode leads.

Acquiring a twelve lead ECG requires the attachment of ten electrodes to a patient. In a first attachment scheme, which is referred to herein as a resting or diagnostic attachment scheme, an attendant (e.g., a doctor, a nurse, an aide, a technician, etc.) places six electrodes on the patient's chest and four electrodes on the patient's limbs. The six electrodes across the chest are known as the V-electrodes (i.e., V1, V2, V3, V4, V5 and V6). The four electrodes attached to the limbs are known as right arm (RA), left arm (LA), left leg (LL) and right leg (RL) electrodes. For diagnostic ECGs the correct placement of the limb electrodes is on the limbs. That is, historically, the limb electrodes were placed at the end of the limbs (e.g., the RA electrode is placed at the right wrist, the RL electrode is placed at the right ankle, etc.). Currently, the limb electrodes are placed more proximal on the limbs.

In a second attachment scheme, which is referred to herein as a monitoring attachment scheme, the attendant places the limb electrodes on the patient's torso. That is, the attendant places the limb electrodes at or proximal to the shoulders and hips. The monitoring attachment scheme includes schemes that are typically referred to as stress, exercise, activity compatible, torso, Mason-Likur, Lund, and/or Krucoff attachment schemes. Placing the limb electrodes onto the patient's torso allows the patient to have more freedom of limb motion. Also, moving the electrodes off of the limbs reduces noise pickup from muscle activity of the limbs.

SUMMARY OF INVENTION

It has become well documented that ECGs recorded using the monitoring attachment scheme can be clinically different from ECGs recorded on the same patients using the diagnostic attachment scheme. These differences can mask real charges or introduce false changes when serial ECGs are compared. Accordingly, it would be beneficial to use an electrode placement that provides ECG recording as much like standard diagnostic ECGs as possible while providing the freedom of motion and reduction of artifact enjoyed by the monitoring attachment scheme.

Accordingly, the invention provides a placement scheme, which is referred to herein as an asymmetrical attachment scheme. For one embodiment of the asymmetrical attachment scheme, the attendant connects the six chest (i.e., "V") electrodes on the patient's chest as normally attached in prior schemes, attaches the right leg electrode on either the limb or the torso, attaches the left leg electrode and right arm electrode on the torso, and the left arm electrode on the limb.

Regardless which attachment scheme is used, occasionally, an attendant incorrectly attaches the electrodes to the patient, or incorrectly connects two or more lead wires to the wrong electrodes. For example, an attendant may incorrectly connect a lead wire to the wrong electrode. The physiological-signal-analysis device expects the lead to be connected to an electrode that is attached at a particular place on the patient's body. This error is referred to herein as lead reversal. A second placement error occurs when the attendant places the electrodes on the wrong spot of the patient's body. This error is referred to herein as a lead placement error. These problems result in the physiological-signal-analysis device acquiring inaccurate or unusable ECGs. Thus, it would be beneficial to have a device to assist the attendant in attaching the electrodes to the patient's body in the correct location, and to assist the attendant in attaching the lead wires to the correct electrodes.

Accordingly, in one embodiment the invention provides a physiological-signal-analysis device including a lead set, and a central unit connected to the lead set. The lead set includes a plurality of electrodes connectable to a patient. Each electrode has a non-alphanumeric symbol that defines a placement of the electrode on the patient in relation to the other electrodes. The lead set further includes a plurality of lead wires. Each lead wire is connected to one of the electrodes, respectively, and has a symbol that defines the electrode connected to the lead wire.

In another embodiment, the invention provides a physiological signal electrode pack having a liner, and first and second electrodes connected to the liner. The first electrode has a first non-alphanumeric symbol, is removable from the liner, and is connectable to a patient. The second electrode has a second non-alphanumeric symbol, is removable from the liner and is connectable to the patient. The second non-alphanumeric symbol defines a placement of the second electrode on the patient in relation to the first electrode. Other embodiments, features and advantages of the invention will become apparent by consideration of the detailed description and accompanying drawings.

BRIEF DESCRIPTION OF DRAWINGS

FIGS. 3–8 are top views of various electrode packs embodying another aspect of the invention.

DETAILED DESCRIPTION

Before any embodiments of the invention are explained, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of including, comprising, or having and variations thereof herein is meant to encompass the items listed thereafter and equivalents thereof as well as additional items.

Figure 1:
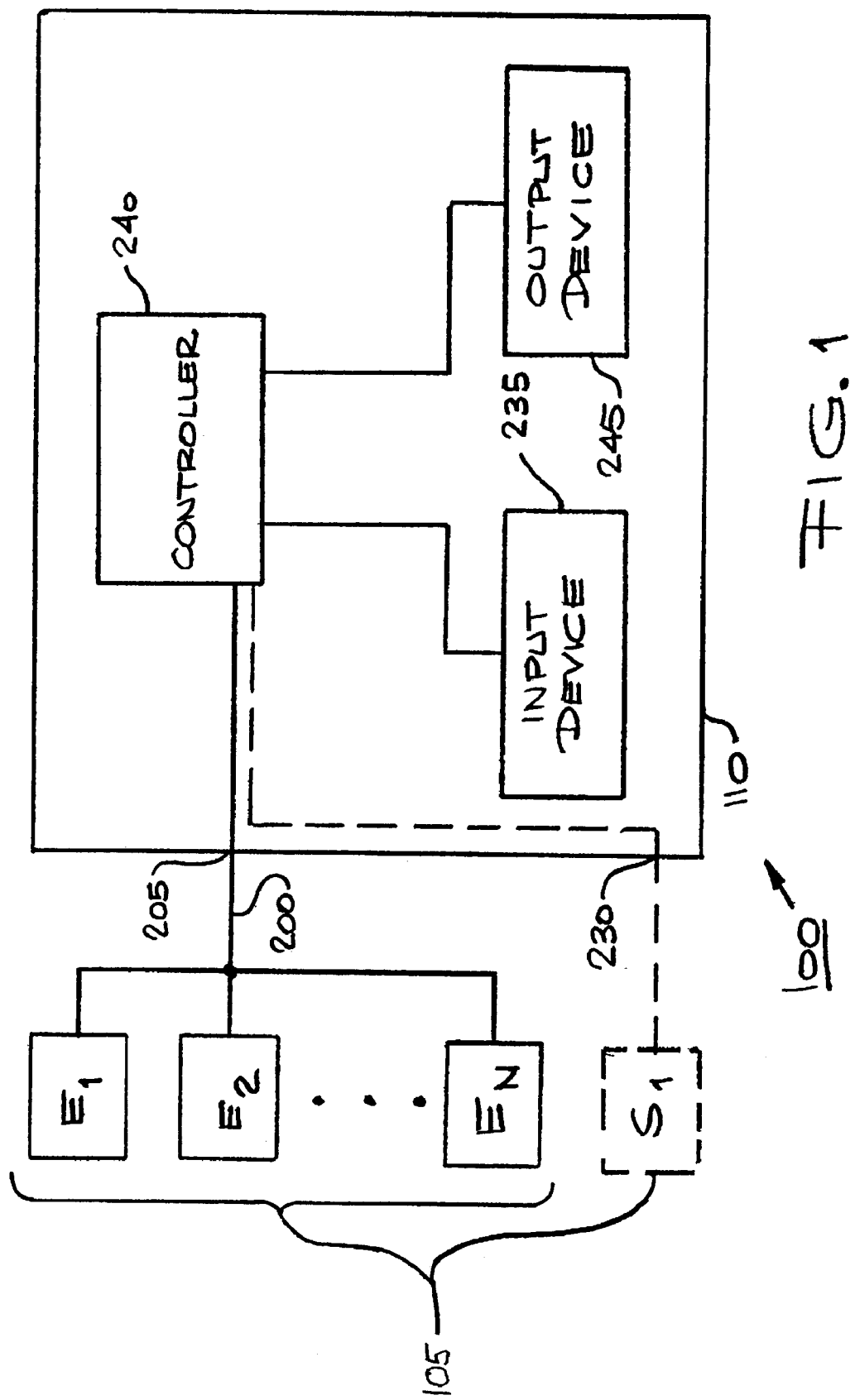
FIG. 1 is a schematic diagram of a physiological signal analysis device.

A physiological-signal-analysis device 100 is schematically shown in FIG. 1. As used herein, the term physiological-signal-analysis device includes any device that, among other things, acquires electrical signals generated by a patient's heart. Example physiological monitoring devices include electrocardiographs (ECG) and patient monitors. It is envisioned that the physiological-signal-analysis device 100 may acquire physiological signals other than the heart's electrical activity. For example, if the physiological-signal-analysis device 100 is a patient monitor, than the monitor may acquire other physiological signals such as a patient's blood pressure, a patient's respiratory function, etc.

In general terms, the device 100 includes one or more physiological-signal-input devices 105 and a central unit 110. The one or more physiological-signal-input devices 105 include a plurality of electrodes $E_1, E_2 \ldots E_n$ that are connectable to a patient, and that sense electrical activity generated by the patient's heart. The number of electrodes $E_1, E_2 \ldots E_n$ and how the electrodes are connected to the patient may vary (e.g., using a standard twelve-lead configuration, using a Frank XYZ ECG configuration, etc.). For the embodiments shown, the number of electrodes is equal to ten, and the electrodes are connected to the patient in a twelve-lead configuration or scheme (discussed further below). Additionally, the type of electrode may vary. A specific embodiment of one electrode is shown in FIG. 2.

Figure 2:
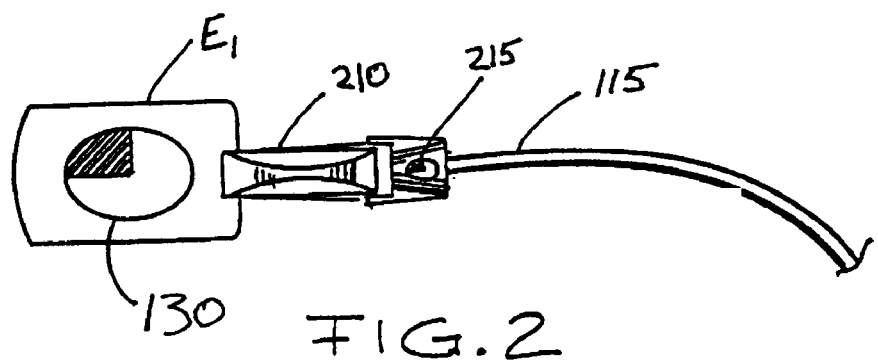
FIG. 2 is a top view of an electrode and lead wire embodying one aspect of the invention.

As shown in FIG. 2, the electrode $E_1$ is a "disposable" electrode that is connected (e.g., attached) to the patient, and the lead wire 115 is connected (e.g., clipped) to the electrode $E_1$. As used herein, the term connection, and variations thereof (e.g., connect, connected, connecting, etc.), includes direct and indirect connections. The connection, unless specified, may be by mechanical, electrical, chemical, and/or electro-magnetic means, or any combination of the foregoing (e.g. electro-mechanical). For the disposable electrode $E_1$ shown, the electrode $E_1$ includes an electrically conductive gel for connecting the electrode to the patient, and for conducting an electrical signal from the patient to the sensor. It is envisioned that in some embodiments of the invention that the electrodes are not disposable.

Figure 3:
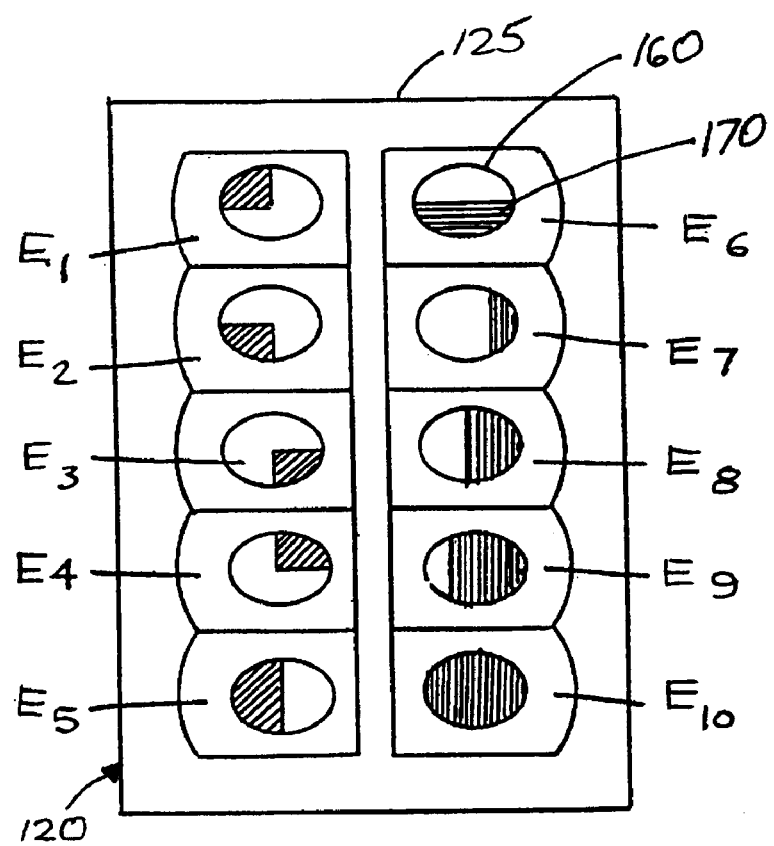
Figure 4:
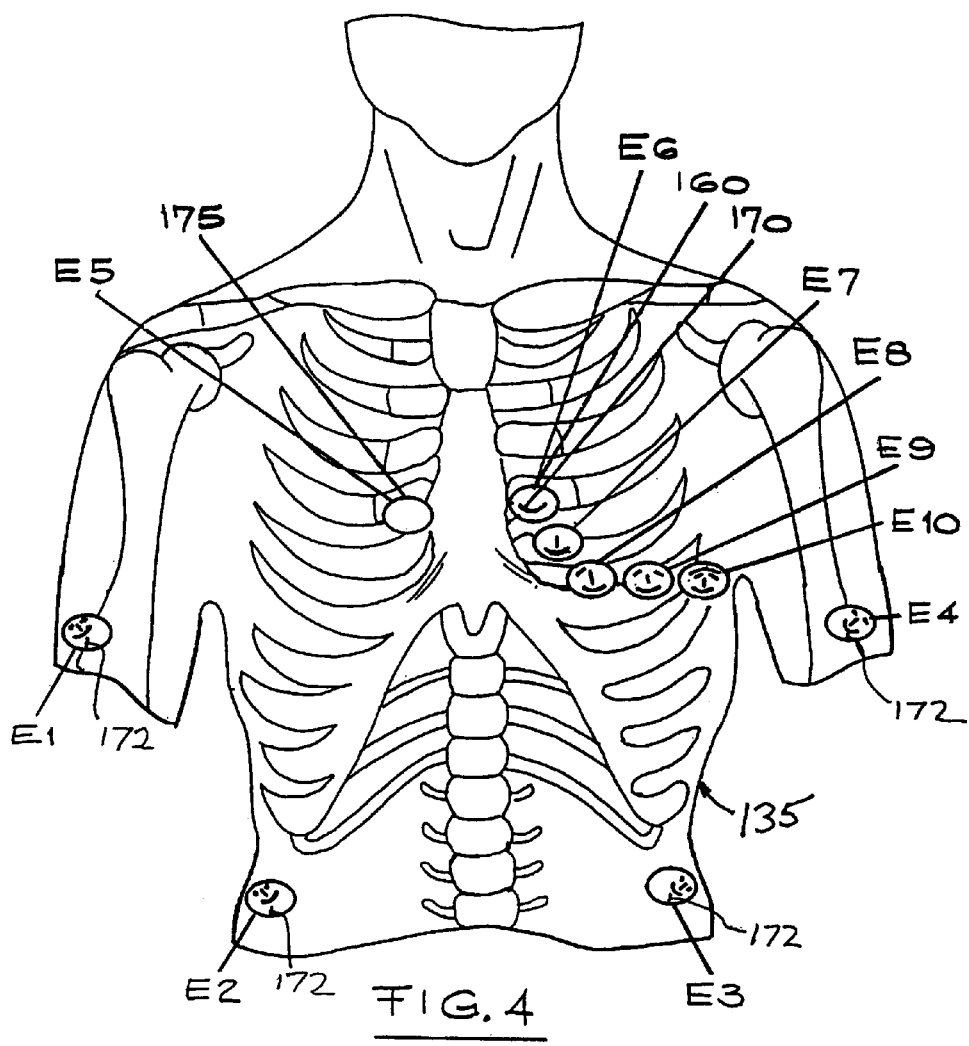
Figure 5:
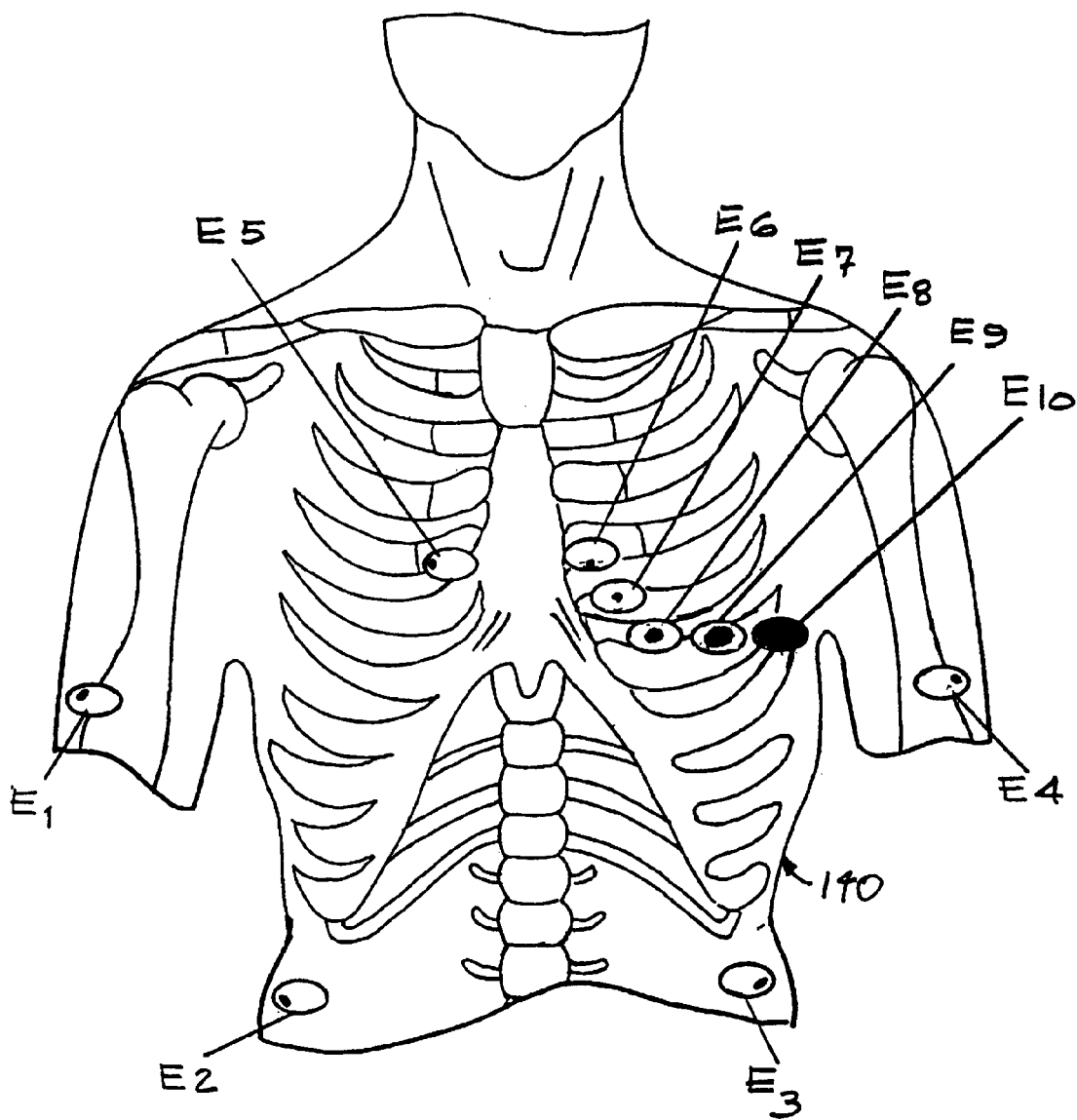

Typically, the electrodes $E_1, E_2 \ldots E_n$ are operationally identical and are provided to the attendant as a pack. For example and as shown in FIG. 3, the pack 120 includes a plurality of electrodes $E_1, E_2 \ldots E_n$ (e.g., ten) connected a liner 125. The liner 125 is of a material that allows the electrodes to release from the liner 125. For example, the electrode $E_1$ may be connected to the liner by the conductive gel such that, when the attendant removes the electrode $E_1$, the electrode $E_1$, including the conductive gel, releases from the liner 120. Furthermore, as shown in FIGS. 4 and 5, the liner 120 may include a pictorial representation of a patient, and/or may be formed as a contoured exterior of the patient. This allows the technician to visualize the expected location of the electrode on the patient.

In attaching the electrodes $E_1, E_2 \ldots E_n$ to the patient, the attendant pulls each electrode $E_1, E_2 \ldots E_n$ from the liner 125 and attaches the electrodes $E_1, E_2 \ldots E_n$ to the patient. To assist the operator in attaching the electrodes $E_1, E_2 \ldots E_n$, each electrode includes a non-alphanumeric symbol or identifier 130 (FIG. 2). As used herein, the term "non-alphanumeric symbol" is defined as something that defines or identifies a placement of the electrode on the patient. That is, each electrode $E_1, E_2 \ldots E_n$ includes a non-alphanumeric symbol 130 that identifies a placement of the electrode (e.g., $E_1$) in relation to the other electrodes (e.g., $E_2 \ldots E_n$).

FIGS. 3–7 show different electrode packs 120, 135, 140, 145, 150 and 155 having a plurality of electrodes $E_1, E_2, E_3, E_4, E_5, E_6, E_7, E_8, E_9,$ and $E_{10}$. The electrode packs 120, 135, 140, 145, 150 and 155 include ten electrodes for a twelve-lead arrangement. Specifically, $E_1, E_2, E_3, E_4$ correspond to right arm (RA), right leg (RL), left leg (LL), and left arm (LA), and $E_5, E_6, E_7, E_8, E_9, E_{10}$ correspond to the chest electrodes V1, V2, V3, V4, V5 and V6. Each electrode $E_1$–$E_{10}$ has a non-alphanumeric symbol (e.g., symbol 130 in FIG. 2).

As shown in FIG. 3, each electrode $E_1$–$E_{10}$ includes a figure (e.g., ellipse 160 for electrode $E_6$) having an indicium (e.g., indicium 170 $E_6$). As used herein, the term indicium means an identifying mark, pattern, design, or configuration that defines an electrode (e.g., electrode $E_6$) in the set of electrodes (e.g., electrodes $E_1$–$E_{10}$). The indicium (e.g., indicium 170) assists the operator in attaching the electrodes to the patient at the correct spots for the electrodes. For the embodiment shown in FIG. 3, the indicium is a shading for the figure, which is used for implying lead order and placement.

As shown in FIG. 4, the indicium (e.g., indicium 170) includes a portion of a face. The use of a face draws on the well-documented human ability to recognize faces. The limb leads have complete faces that "face the heart" when placed in the proper orientation. The V-leads have a face that acquires more detail as it moves from left to right. Additionally, the leads may include a "pointer" or "reference" to help provide orientation for the electrode. For example and as shown in FIG. 4, marking 172 helps provide an orientation for the electrodes ($E_1, E_3, E_3, E_4$). It is envisioned that for one of the electrodes (e.g., electrode 175 in FIG. 4) the electrode may not include any markings (i.e., the lack of the marking is the indicium). In other embodiments, a scene of photographic image is printed on the electrodes so that the scene is visible when the electrodes are properly aligned.

For FIG. 5, the indicium includes a dot where the dot varies in location and in size. For FIG. 6, the indicium includes at least one dot where the number of dots and/or the placement of the dots may vary. For FIG. 7, the indicium is a configuration of the figure. For FIG. 8, the indicia are similar to the indicia for FIG. 6, but the non-alphanumeric symbol does not include the figure. It is also envisioned that the electrode may include alphanumeric identifiers (see, e.g., FIG. 7) for further assisting the attendant in attaching the electrodes to the patient. However, for embodiments including the alphanumeric identifiers, at least two of the electrodes include non-alphanumeric symbols. Further, it is envisioned that industry standard labeling, including color coding, may be added to the electrodes $E_1, E_2 \ldots E_n$.

Referring back to FIGS. 1 and 2, the electrodes $E_1, E_2 \ldots E_n$ are connected to the central unit 110 by an interface cable 200. The electrodes $E_1, E_2 \ldots E_n$ and the interface cable 200 form a lead set. The interface cable 200 provides direct communication between the electrodes $E_1, E_2 \ldots E_n$ and an input terminal 205. The interface cable 200 allows for transmission of the sensed ECG signals from the patient to the central unit 110. The interface cable 200 is preferably a passive cable but, alternatively, the cable 200 may contain active circuitry for amplifying and combining the ECG signals into ECG leads. The interface cable 200 includes a plurality of lead wires (e.g., wire 115) that are connected to respective electrodes via a clip 210. As shown in FIG. 2, the clip 210 may also include a non-alphanumeric symbol or identifier 215. The non-alphanumeric symbol 215 allows the operator to connect the lead wire to the correct electrode. In one embodiment, the non-alphanumeric symbols on the clips of the lead wires correspond to the non-alphanumeric symbols on the electrodes. Therefore, the operator can correctly place the electrodes $E_1, E_2 \ldots E_n$ on the patient using the non-alphanumeric symbols, and correctly attach the lead wires 115 to the electrodes using the non-alphanumeric symbols on the clips 210. It is envisioned that other fastening devices may be used to connect the lead wires to the electrodes, and that the non-alphanumeric symbols may be placed elsewhere (e.g., directly on the lead wires).

In other embodiments, the electrodes $E_1, E_2 \ldots E_n$ may be in communication with the central unit 110 through a telemetry-based transmitter that transmits radio frequency ("RF") signals to one or more antennas connected to the central unit 110. In yet other embodiments, the lead wires are directly connected to the device 100 (i.e., the wires are not "combined" into an interface cable as shown in FIG. 1).

As shown in FIG. 1, the physiological-analysis device 100 may further include other physiological sensors (e.g., sensor $S_1$) The sensor $S_1$ is connectable to the patient and acquires physiological signals from the patient. For example, the sensor $S_1$ may be a noninvasive blood pressure sensor, a carbon dioxide sensor, a pulse-oximetry sensor, a temperature sensor, etc. Similar to electrodes $E_1$, $E_2$ . . . $E_n$ and for the embodiment shown, the sensor $S_1$ is connected to the central processing unit 110 at input terminal 230.

The central unit 110 may be any central unit that receives the physiological signals, processes and/or analyzes the signals, and communicates the processed signals and/or outputs the resulting analysis. For the embodiment shown, the central unit includes one or more operator-controlled-input devices 235, a controller 240, and one or more output devices 245. The operator-controlled-input devices 245 allow an operator (e.g., a technician, nurse, doctor, etc.) to control the physiological-signal-analysis device 100 and/or to provide data to the central unit 110. The operator-controlled-input devices 245 may be incorporated within the central unit 110 (e.g., one or more push buttons, one or more trim knobs, a pointing device, a keyboard etc.) or, alternatively, may be stand-alone devices (e.g., a stand-alone keyboard, etc.). Example operator-controlled-input devices 115 include a trim knob, a keyboard, a keypad, a touch screen, a pointing device (e.g., a mouse, a trackball), etc.

The controller 240 receives input signals from the one or more physiological-signal-input devices 105, and the one or more operator-controlled-input devices 235. The input signals include input or data. The controller 240 analyzes the inputs, and communicates output signals to the one or more output devices 245. The output signals include output or data.

In one embodiment, the controller 240 includes a processor and a memory. The memory includes one or more software modules having instructions, and the processor retrieves, interprets, and executes the instructions of the one or more software modules to control the device 100. However, it is envisioned that other controllers may be used with the invention. For example, the controller 240 may be constructed with other analog and/or digital logic circuitry, and may include integrated and/or discrete circuit elements. In addition, the controller 240 may include other elements (e.g., one or more analog-to-digital converters, one or more drivers, one or more power supplies, one or more amplifiers, one or more filters, etc.) that would be apparent to one skilled in the art to support the controller 240.

The one or more output devices 245 receive output signals from the controller 240 and provide an interface to the attendant. The output devices 245 may include a printer, a display, a storage device (e.g., a magnetic-disc drive, a read/write CD-ROM, etc.), a server or other processing unit connected via a network. Of course, other output devices may be added or attached (e.g., an audio-output device). Additionally, not all of the output devices are required for operation of the physiological-signal-analysis device 100.

Figure 9:
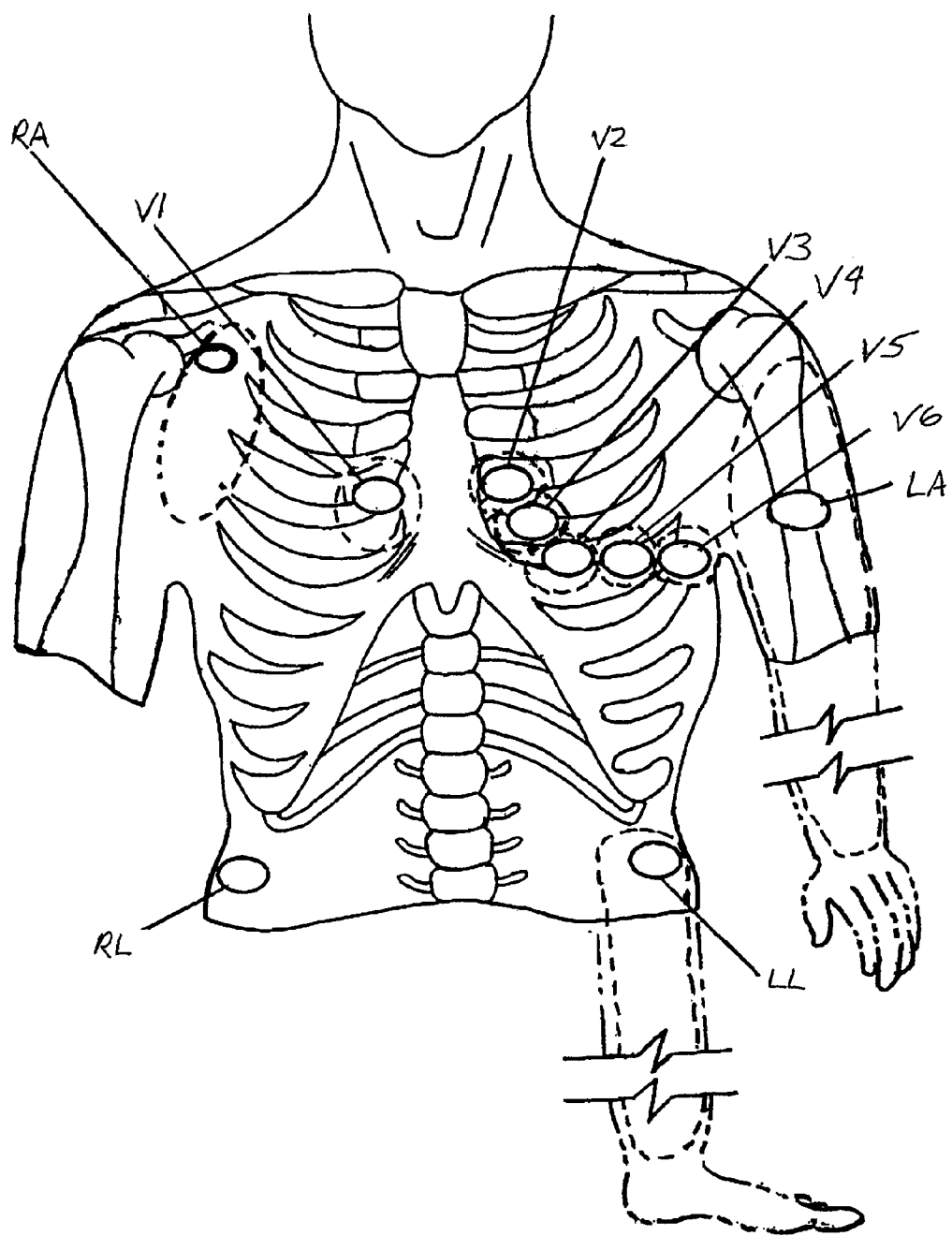
FIG. 9 is a schematic diagram of a placement scheme embodying yet another aspect of the invention.

In operation, an attendant obtains an electrode pack (e.g., pack 120), removes the electrodes from the liner 125, and places the electrodes on the patient. In one embodiment, the attendant places the electrodes $E_1$–$E_{10}$ on the patient in an asymmetrical configuration. The asymmetrical configuration is schematically shown in FIG. 9.

The asymmetrical attachment scheme uses ten electrodes and generates twelve ECG leads. Six electrodes are placed on the chest and are referred to as the V1, V2, V3, V4, V5 and V6 electrodes. The terms V1, V2, V3, V4, V5 and V6 are used for the description herein, and other terms or descriptors may be used.

In one embodiment, the V1 electrode is placed at approximately the fourth intercostal space at the right border of the sternum. The V2 electrode is placed at approximately the fourth intercostal space at the left border of the sternum. The V4 electrode is placed at approximately the fifth intercostal space in the left midclavicular line. The V3 electrode is placed at approximately midway between locations V2 and V4. The V5 electrode is placed at approximately the anterior axillary line and on the same horizontal level as V4. As used herein, the term horizontal refers to a line perpendicular to the axis of the spine, as though the subject was standing. In other embodiments, the V5 electrode is specified as midway between V4 and V6 electrodes. The V6 electrode is placed at approximately the midaxillary line on the same horizontal level as V4 and V5.

In addition to the six chest electrodes, four additional electrodes are placed on the patient's body. These four electrodes are referred to as the RA, RL, LL, and LA electrodes. The terms RA, RL, LL and LA are used for the description herein, and other terms or descriptors may be used (e.g., first, second, third and fourth electrodes). The RA electrode is placed in a range approximately from the right side infraclavicular fossae, in a range from 2 cm below the lower border of the clavicle (i.e., collarbone) and medial to the border of the deltoid muscle, to distal and below the outer clavicle. As used herein, the terms left and right refer to patient's left and right. The LL electrode is placed in a range approximately from the left lower abdomen below the level of the umbilicus (i.e., the navel), in the anterior axillary line, midway between the rib margin and the iliac spine, to the left ankle. The LA electrode is placed in a range approximately from the left wrist (including the left wrist) to the left axilla (i.e., armpit). The RL electrode is placed anywhere on the body, but not immediately next to other electrodes. Thus, the LA electrode is placed on the limb while the RA, LL and RL electrodes are placed on the patient's torso. This results in an attachment scheme that allows the patient some increased freedom of motion and reduced artifact generation, as compared to the diagnostic attachment scheme, and reduced distortion or clinical difference, as compared to the monitoring attachment scheme. In a preferred embodiment, the RA electrode is placed at approximately the right side infraclavicular fossae, in a range from 2 cm below the lower border of the clavicle and medial to the border of the deltoid muscle. The LL electrode is placed at approximately the left lower abdomen below the level of the umbilicus, in the anterior axillary line, midway between the rib margin and the iliac spine. The LA electrode is placed at the outside or front of the arm just off of the shoulder, but not on a muscle. The RL is placed anywhere on the torso, but not immediately next to other electrodes.

Thus, the invention provides, among other things, a new and useful physiological-signal-analysis device having a plurality of electrode leads. Various features and advantages of the invention are set forth in the following claims.

What is claimed is:

1. A physiological-signal-analysis device comprising:
   a lead set including
      a plurality of electrodes connectable to a patient, each of the plurality of electrodes having a respective non-alphanumeric symbol that defines a placement of the electrode on the patient in relation to the other electrodes, and a plurality of lead wires, each lead wire being connected to one of the electrodes, respectively; and a central unit connected to the lead set.

2. A device as set forth in claim 1 wherein the lead set includes an interface cable, wherein the interface cable includes the plurality of lead wires, and wherein the interface cable connects the plurality of electrodes to the central unit.

3. A device as set forth in claim 1 wherein each non-alphanumeric symbol includes an indicium for each electrode, respectively.

4. A device as set forth in claim 3 wherein each indicium is a photographic image.

5. A device as set forth in claim 1 wherein each non-alphanumeric symbol includes a figure.

6. A device as set forth in claim 5 wherein each figure includes an indicium.

7. A device as set forth in claim 6 wherein each indicium includes a portion of the figure being shaded.

8. A device as set forth in claim 6 wherein each indicium includes at least a portion of a face.

9. A device as set forth in claim 6 wherein each indicium includes at least one dot.

10. A device as set forth in claim 9 wherein each indicium varies the at least one dot by at least one of size, number, or location.

11. A device as set forth in claim 1 wherein the device is an electrocardiogram.

12. A device as set forth in claim 1 wherein the device is a patient monitor, and wherein the electrodes are disposable electrocardiogram electrodes.

13. A physiological-signal-analysis device comprising:

a lead set including a plurality of electrodes connectable to a patient, at least two of the plurality of electrodes having a respective non-alphanumeric symbol that defines a placement of the at least two electrodes on the patient in relation to each other, each non-alphanumeric symbol including a respective indicium, each indicium including at least a portion of the indicium being shaded, and a plurality of lead wires, each lead wire being connected to one of the electrodes, respectively; and a central unit connected to the lead set.

14. A device as set forth in claim 13 wherein each indicium varies the at least one dot by at least one of size, number or location.

15. A physiological signal electrode pack comprising:

a liner; and a plurality of electrodes connected to the liner, each electrode having a respective non-alphanumeric symbol, being removable from the liner, and being connectable to a patient, each non-alphanumeric symbol defining a placement of the respective electrode on the patient in relation to the other electrodes.

16. An electrode pack as set forth in claim 15 wherein the electrodes are electrocardiogram electrodes.

17. An electrode pack as set forth in claim 15 wherein each non-alphanumeric symbol is unique for the respective electrode.

18. An electrode pack as set forth in claim 15 wherein the each non-alphanumeric symbol includes at least one dot.

19. An electrode pack as set forth in claim 18 wherein each non-alphanumeric symbol varies the at least one dot by at least one of size, number, or location.

20. An electrode pack as set forth in claim 15 wherein each non-alphanumeric symbol includes a figure.

21. An electrode pack as set forth in claim 20 wherein each figure includes a respective indicium.

22. An electrode pack as set forth in claim 21 wherein each indicium includes a portion of the figure being filled.

23. An electrode pack as set forth in claim 21 wherein each indicium includes at least a portion of a face.

24. An electrode pack as set forth in claim 21 wherein each indicium includes at least one dot.

25. An electrode pack as set forth in claim 24 wherein each indicium varies the at least one dot by at least one of size, number, or location.

26. An electrode pack as set forth in claim 20 wherein each indicium includes a portion of the figure being shaded.

27. A method of acquiring a twelve-lead electrocardiogram (ECG) from a patient, the method comprising:

providing a physiological-signal-analysis device;

providing ten electrodes;

connecting the ten electrodes to the patient including placing a first electrode in a first area, the first area being approximately from the right side infraclavicular fossae, in a range two centimeters below the lower border of the clavicle and medial to the border of the deltoid muscle, to distal and below the outer clavicle, placing a second electrode in a second area, the second area being approximately from the left lower abdomen below the level of the umbilicus, in the anterior axillary line, midway between the rib margin and the iliac spine, to the left ankle, placing a third electrode in a third area, the third area being approximately from the left wrist, including the left wrist, to the left axilla, and placing a fourth electrode on the patient; and connecting the ten electrodes to the physiological-signal analysis device.

28. A method as set forth in claim 27 wherein the act of connecting the ten electrodes to the patient further includes placing the fifth, sixth, seventh, eighth, ninth, and tenth electrodes on the patient.

29. A physiological-signal-analysis device comprising:

a lead set including a plurality of electrodes connectable to a patient, the plurality of electrodes including a first electrode having a first non-alphanumeric symbol and a second electrode having a second non-alphanumeric symbol, the first and second non-alphanumeric symbols defining a placement of the first and second electrodes on the patient in relation to each other, and a plurality of lead wires connected to the plurality of electrodes, the plurality of lead wires including a first lead wire having a first symbol that defines connecting the first lead wire to the first electrode and a second lead wire having a second symbol that defines connecting the second lead wire to the second electrode; and a central unit connected to the lead set.

30. A device as set forth in claim 29 wherein the symbols of the plurality of lead wires are non-alphanumeric symbols.

31. A device as set forth in claim 30 wherein the non-alphanumeric symbols of the plurality of lead wires are the same as the non-alphanumeric symbols of the respective electrodes connected to the lead wires.

32. A device as set forth in claim 31 wherein each of the plurality of electrodes have a respective alphanumeric symbol and each of the plurality of lead wires have a respective alphanumeric symbol.

33. A physiological-signal-analysis device comprising:

a lead set including a plurality of electrodes connectable to a patient, at least two of the plurality of electrodes having a respective non-alphanumeric symbol that defines a placement of the at least two electrodes on the patient in relation to each other, each non-alphanumeric symbol including a respective indicium, each indicium including at least a portion of the indicium being shaded, and a plurality of lead wires, each lead wire being connected to one of the electrodes, respectively; and a central unit connected to the lead set.

34. An electrode pack comprising:

a liner; and first, second, third, fourth, fifth, sixth, seventh, eighth, ninth and tenth electrodes connected to the liner, each electrode having a respective non-alphanumeric symbol, being removable from the liner, and being connectable to a patient, the first, second, third, fourth, fifth, sixth, seventh, eighth, ninth and tenth non-alphanumeric symbols defining a placement of the respective electrode on the patient in relation to the other electrodes.

* * * * *